(12) United States Patent
Tass et al.

(10) Patent No.: US 10,722,678 B2
(45) Date of Patent: Jul. 28, 2020

(54) DEVICE AND METHOD FOR EFFECTIVE NON-INVASIVE TWO-STAGE NEUROSTIMULATION

(71) Applicant: Forschungszentrum Juelich GmbH, Juelich (DE)

(72) Inventors: Peter Alexander Tass, Tegernsee (DE); Magteld Zeitler, Malden (NL)

(73) Assignee: Forschungszentrum Juelich GmbH, Juelich (DE)

( * ) Notice: Subject to any disclaimer, the term of this patent is extended or adjusted under 35 U.S.C. 154(b) by 278 days.

(21) Appl. No.: 15/738,693

(22) PCT Filed: Jun. 22, 2016

(86) PCT No.: PCT/EP2016/064472
§ 371 (c)(1),
(2) Date: Dec. 21, 2017

(87) PCT Pub. No.: WO2016/207247
PCT Pub. Date: Dec. 29, 2016

(65) Prior Publication Data
US 2018/0169373 A1 Jun. 21, 2018

(30) Foreign Application Priority Data
Jun. 22, 2015 (DE) .................. 10 2015 109 986

(51) Int. Cl.
*A61N 5/10* (2006.01)
*G06N 99/00* (2019.01)
(Continued)

(52) U.S. Cl.
CPC ........... *A61M 21/02* (2013.01); *A61B 5/0476* (2013.01); *A61B 5/0488* (2013.01);
(Continued)

(58) Field of Classification Search
CPC ............... A61N 2/006; A61N 1/36014; A61N 1/36025; A61N 1/36064; A61N 1/36067;
(Continued)

(56) References Cited

U.S. PATENT DOCUMENTS

2017/0151436 A1* 6/2017 Flaherty ............... A61N 5/0622

FOREIGN PATENT DOCUMENTS

DE 102008052078 A1 4/2010
DE 102009015723 A1 12/2010
(Continued)

OTHER PUBLICATIONS

Reversing Pathologically Increased EEG Power by Acoustic Coordinated Reset Neuromodulation, Ilya Adamchic et al., Human Brain Mapping 35:2099-2118 (2014).
(Continued)

*Primary Examiner* — Christine H Matthews
*Assistant Examiner* — Joshua Daryl D Lannu
(74) *Attorney, Agent, or Firm* — Arent Fox LLP

(57) ABSTRACT

A device for stimulating neurons that includes a noninvasive stimulation unit for generating stimuli in stimulation channels. A control unit controls the stimulation unit during first and second time intervals in different stimulation modes. The control unit controls the stimulation unit during 75% or more of the first time interval in the first stimulation mode to repeatedly generate sequences of stimuli and the order in which the stimulation channels generate stimuli is constant for not more than 5 successively generated sequences and then varied. The control unit controls the stimulation unit during 75% or more of the second time interval in a second stimulation mode such that the stimulation channels repeatedly generate sequences of stimuli and
(Continued)

the order in which the stimulation channels generate stimuli is constant for at least 25 successively generated sequences and then varied.

18 Claims, 6 Drawing Sheets

(51) Int. Cl.
    *G06N 7/00*    (2006.01)
    *G06N 5/04*    (2006.01)
    *A61B 6/03*    (2006.01)
    *A61M 21/02*    (2006.01)
    *A61N 2/00*    (2006.01)
    *A61B 5/0476*    (2006.01)
    *A61B 5/0488*    (2006.01)
    *A61N 1/36*    (2006.01)
    *A61B 5/00*    (2006.01)
    *A61B 5/11*    (2006.01)
    *A61B 5/053*    (2006.01)
    *A61M 21/00*    (2006.01)
    *A61N 2/02*    (2006.01)

(52) U.S. Cl.
    CPC .......... *A61B 5/0531* (2013.01); *A61B 5/1101* (2013.01); *A61B 5/4035* (2013.01); *A61B 5/4836* (2013.01); *A61B 5/6868* (2013.01); *A61N 1/361* (2013.01); *A61N 1/36014* (2013.01); *A61N 1/36025* (2013.01); *A61N 1/36064* (2013.01); *A61N 1/36067* (2013.01); *A61N 1/36082* (2013.01); *A61N 1/36103* (2013.01); *A61N 1/36139* (2013.01); *A61N 1/36175* (2013.01); *A61N 1/36178* (2013.01); *A61N 2/006* (2013.01); *A61B 5/0533* (2013.01); *A61B 5/4064* (2013.01); *A61B 5/4082* (2013.01); *A61B 5/4088* (2013.01); *A61B 5/4094* (2013.01); *A61B 5/686* (2013.01); *A61B 2562/0219* (2013.01); *A61M 2021/0022* (2013.01); *A61M 2021/0027* (2013.01); *A61M 2021/0044* (2013.01); *A61M 2021/0055* (2013.01); *A61M 2021/0066* (2013.01); *A61M 2021/0072* (2013.01); *A61M 2230/10* (2013.01); *A61M 2230/60* (2013.01); *A61N 1/36021* (2013.01); *A61N 2/002* (2013.01); *A61N 2/02* (2013.01)

(58) Field of Classification Search
    CPC ................ A61N 1/36082; A61N 1/361; A61N 1/36103; A61N 1/36139; A61N 1/36175; A61N 1/36178; A61N 1/36021; A61N 2/002; A61N 2/02; A61B 5/0476; A61B 5/0488; A61B 5/4064; A61B 5/4082; A61B 5/4088; A61B 5/4094; A61B 5/4836; A61B 2562/0219; A61B 5/686; A61B 5/6868; A61B 5/0533; A61B 5/1101; A61B 5/4035; A61B 5/0531; A61M 2021/0022; A61M 2021/0027; A61M 2021/0055; A61M 2021/0066; A61M 2021/0072; A61M 21/02; A61M 2230/10; A61M 2230/60; A61M 2230/005; A61M 2021/0044
    See application file for complete search history.

(56) References Cited

FOREIGN PATENT DOCUMENTS

| | | |
|---|---|---|
| DE | 102010016461 A1 | 10/2011 |
| DE | 102010016404 A1 | 12/2012 |

OTHER PUBLICATIONS

Impact of acoustic coordinated reset neuromodulation on effective connectivity in a neural network of phantom sound, Alexander N. Silchenko et al. NeuroImage 77 (2013) 133-147.

Counteracting tinnitus by acoustic coordinated reset neuromodulation, Tass et al. Restorative Neurology and Neuroscience 30 (2012) 137-159.

Abnormal cross-frequency coupling in the tinnitus network, Ilya Adamchic et al., Frontiers in Nueroscience, Sep. 2014 | vol. 8 | Article 284.

* cited by examiner

DEVICE AND METHOD FOR EFFECTIVE NON-INVASIVE TWO-STAGE NEUROSTIMULATION

CROSS-REFERENCE TO RELATED APPLICATIONS

This application is a National Stage entry of International Application No. PCT/EP2016/064472, filed on Jun. 22, 2016, which claims priority to German Application No. 10 2015 109 986.1, filed on Jun. 22, 2015, the contents of each of these priority applications are hereby incorporated by reference in their entirety.

TECHNICAL FIELD

The invention relates to a device and a method for effective non-invasive two-stage neurostimulation by means of varying stimulus sequences.

BACKGROUND

In patients with neurological or psychiatric disorders, e.g. Parkinson's disease, essential tremor, dystonia, functional disorders after stroke, migraine, obsessive-compulsive disorders, epilepsy, tinnitus, schizophrenia, depression, borderline personality disorder and irritable bowel syndrome, nerve cell clusters in distinct regions of the brain are active in a pathologically synchronous manner. In this case, a large number of neurons synchronously form action potentials, i.e. the involved neurons fire in an excessively synchronous manner. In healthy persons, however, the neurons in these brain regions fire qualitatively differently, e.g. in an uncorrelated manner.

In Parkinson's disease, the pathologically synchronous activity in the thalamus and in the basal ganglia changes the neuronal activity in other brain regions, e.g. in areas of the cerebral cortex, such as the primary motor cortex. Here, the pathologically synchronous activity in the region of the thalamus and of the basal ganglia enforces its rhythm e.g. on the cerebral cortex areas, so that finally the muscles controlled by these areas display a pathological activity, e.g. a rhythmic trembling (tremor). In the case of a chronic subjective tinnitus, pathologically synchronous activity is found in a network of auditory and non-auditory brain areas.

In patients with brain diseases and spinal cord diseases, which are characterized by excessively synchronized neuronal activity, non-invasively determined spatiotemporal stimulus patterns, in particular the "coordinated reset" stimulation (CR stimulation), are applied in order to achieve permanent alleviation. The non-invasive CR stimulation can be realized by means of different stimulation modes:
(i) by sensory stimulation, i.e. by physiological stimulation of receptors, such as e.g. acoustic stimulation of the inner ear, visual stimulation of the retina or mechanical (e.g. vibrotactile) or thermal stimulation of skin, subcutaneous, muscle and tendon receptors;
(ii) by stimulation of peripheral nerves (and associated receptors), e.g. by means of electric current (e.g. transcutaneous electrical stimulation), by means of magnetic fields (transdermal magnetic stimulation) or by means of ultrasound; and
(iii) by stimulation of the brain or spinal cord, e.g. by means of electric current (e.g. external cranial or transcranial neurostimulation), by means of magnetic fields (e.g. transcranial magnetic stimulation) or by means of ultrasound.

Acoustic CR stimulation is used to treat the chronic subjective tonal or narrow-band tinnitus. To this end, therapy tones are adapted to the dominant tinnitus tone and are applied for the purpose of CR stimulation in order to achieve a long-lasting desynchronization of the pathologically synchronous activity, which significantly exceeds the switch-off of the stimulation, or even a continuous desynchronization thereof. Acoustic CR stimulation for treating tinnitus brings about a significant and clearly marked reduction of symptoms (cf. P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012)), a significant reduction in the pathological neuronal synchronization in a network of auditory and non-auditory brain areas (cf. P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012); I. Adamchic, T. Toth, C. Hauptmann, P. A. Tass: Reversing pathologically increased EEG power by acoustic CR neuromodulation. Human Brain Mapping 35, 2099-2118 (2014)), a significant reduction in the pathological interactions between different brain areas in the same (cf. A. N. Silchenko, I. Adamchic, C. Hauptmann, P. A. Tass: Impact of acoustic coordinated reset neuromodulation on effective connectivity in a neural network of phantom sound. Neuroimage 77, 133-147 (203)) as well as in different (cf. Adamchic, B. Langguth, C. Hauptmann, P. A. Tass: Abnormal brain activity and cross-frequency coupling in the tinnitus network. Frontiers in Neuroscience 8, 284 (2014)) frequency ranges.

In an analogous manner, Parkinson's disease can be treated by means of vibrotactile CR stimulation. Further indications are, for example, epilepsy, functional disorders after stroke, chronic pain syndromes (by means of vibrotactile and/or thermal CR stimulation), migraine (e.g. by means of visual CR stimulation). Furthermore, these diseases can be treated with transcranial magnetic stimulation or direct electrical stimulation of the brain or direct brain stimulation by means of ultrasound.

In all three above-mentioned stimulation modalities (i) to (iii), low stimulus intensities should be used for stimulation in order to avoid disadvantages (for different reasons described in the following). However, this should not lead to a reduction in the effectiveness of the stimulation nor to an extension of the stimulation duration.

(i) Sensory stimulation: In sensory stimulation, it is important that the desired stimulation effects, e.g. a phase resetting of the pathologically synchronized oscillatory activity in the brain or spinal cord, can be achieved at all with the lowest possible stimulus intensity. For example, in acoustic CR stimulation for the treatment of tinnitus, typically hearing-impaired patients have to be treated. Stimulation with loud tones can damage the inner ear, can make a communication with others more difficult, and can cover warning sounds such as a vehicle horn or bicycle bell, or can be perceived as clearly unpleasant by the patient as a result of the intolerability threshold being comparatively close to the hearing threshold. The acoustic stimulation of tinnitus patients with hyperacusis can be particularly problematic, since such patients perceive acoustic stimulation partly as unpleasant or even unbearable. In addition, in the case of hearing-impaired tinnitus patients, the loud stimulation can also be heard and be perceived as disturbing by the patient's environment. In the visual CR stimulation, unpleasant glare effects can occur in particular in the case of migraine patients. In the case of a mechanical, e.g. vibrotactile or thermal CR stimulation of patients with chronic pain syndromes, e.g. with Sudeck's disease or neuralgias, even slight touching or thermal stimuli can be perceived as unpleasant or even painful. If, in such cases, treatment has to occur via the contralateral extremity or face or body half, the stimulatory effect is not strongly pronounced as a result of the application in the healthy body half. All in all, it is very advantageous in sensory CR stimulation if very low stimulus intensities can be used for stimulation, since sensory stimuli, such as tones, brightness fluctuations of transmission glasses, etc. can interfere with the physiological stimulus processing.

(ii) Electrical or magnetic stimulation of peripheral nerves: In order to be able to stimulate as focally as possible and to prevent side effects that are caused by the simultaneous stimulation of adjacent structures, e.g. muscle contractions, pain sensations, etc., it is important that the smallest possible stimulus intensities be used.

(iii) Electrical or magnetic stimulation of the brain or spinal cord: Both stimulation forms are not very focal. For example, even in the most favorable case of stimulation via a plurality of small electrodes and when using complex head models, in addition to a strong focal stimulation, direct electrical stimulation of the brain leads to an accompanying stimulation of far-stretched brain regions, which should be avoided or reduced particularly in the case of chronic irritation. In the same way, ultrasonic stimulation should be limited to the actual target regions in the brain.

In all of these cases, it is therefore necessary to be able to perform the treatment with the smallest possible stimulus intensities in order to reduce the undesired simultaneous stimulation of non-target areas. However, this often leads to the fact that the treatment is not sufficiently effective.

SUMMARY

It is the object of the invention to provide a device and a method for stimulating neurons, with which robust therapeutic effects can be achieved despite reduced stimulus intensity and without a significantly increased stimulation duration.

The object of the invention is achieved by the features of the independent claims. Advantageous embodiments and further developments of the invention are specified in the dependent claims.

BRIEF DESCRIPTION OF THE DRAWINGS

The invention will be explained by way of example in more detail below with reference to the drawings, which show.

DETAILED DESCRIPTION

Figure 1:
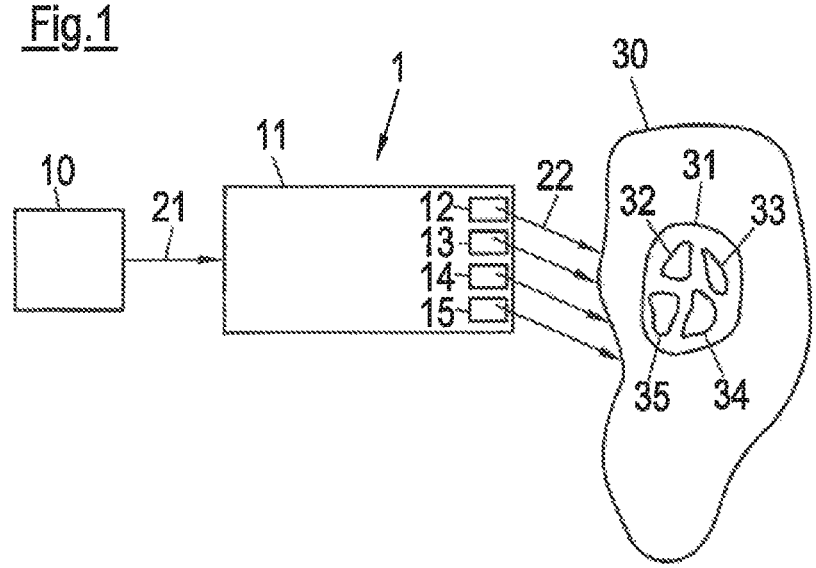
FIG. 1 illustrates a schematic illustration of a device for suppressing a pathologically synchronous and oscillatory neuronal activity and in particular for desynchronization of neurons having a pathologically synchronous and oscillatory activity according to a first embodiment.

FIG. 1 schematically illustrates a device 1 for stimulating neurons having a pathologically synchronous and oscillatory neuronal activity. The device 1 consists of a control unit 10 and a stimulation unit 11, which stimulates neurons in the brain and/or spinal cord 30 of a patient via a plurality of stimulation channels. Each stimulation channel enables the stimulation of another target region in the brain and/or spinal cord 30 of the patient, wherein the target regions associated with the stimulation channels are not necessarily disjunct, i.e. do not have to be completely separated from one another, but can also overlap one another. FIG. 1 exemplarily illustrates the stimulation via four stimulation channels 12, 13, 14 and 15. Of course, stimulation can also take place via a different number of stimulation channels, e.g. 2, 3, 5, 6, etc.

During the operation of the device 1, the control unit 10 performs a control of the stimulation unit 11. To this end, the control unit 10 generates control signals 21 that are received by the stimulation unit 11.

The stimulation unit 11 generates stimuli 22 in the stimulation channels 12 to 15 on the basis of the control signals 21, which are administered to the patient. The stimuli 22 may be sensory stimuli, e.g. acoustic, visual, tactile, vibratory, thermal, olfactory, gustatory, transcutaneous electrical, transcutaneous magnetic, transcranial electrical and/or transcranial magnetic stimuli and/or ultrasonic stimuli. In particular tactile and vibratory stimuli 22 are also applied together and are then referred to as vibrotactile stimuli 22. The stimuli 22 can be perceived by the patient in particular in a conscious manner. The stimuli 22 are designed, upon administration to the patient via the stimulation channels 12 to 15, to suppress the pathologically synchronous and oscillatory neuronal activity and in particular to desynchronize the neurons having the pathologically synchronous and oscillatory activity.

The stimulation unit 11 and in particular also the control and analysis unit 10 are non-invasive units, i.e., during the operation of the device 1, they are located outside the patient's body and are not surgically implanted in the patient's body.

The device 1 and the device 2 described further below in connection with FIG. 4 can in particular be used for treating neurological or psychiatric disorders, e.g. Parkinson's disease, essential tremor, tremor as a result of multiple sclerosis and other pathological tremors, dystonia, epilepsy, depression, movement disorders, cerebellar disorders, obsessive-compulsive disorders, dementia, Alzheimer's disease, Tourette's syndrome, autism, functional disorders after stroke, spastics, tinnitus, sleep disorders, schizophrenia, irritable bowel syndrome, addiction, borderline personality disorder, attention deficit syndrome, attention deficit hyperactivity syndrome, gambling addiction, neuroses, bulimia, anorexia, eating disorders, burnout syndrome, fibromyalgia, migraine, cluster headache, general headache, neuralgia, ataxia, tic disorder or hypertension, and further disorders characterized by pathologically increased neuronal synchronization.

The aforementioned diseases can be caused by a disruption of the bioelectric communication of neuron clusters, which are combined in specific circuits. In this case, a neuron population persistently generates pathological neuronal activity and possibly a pathological connectivity associated therewith (network structure). Here, a large number of neurons synchronously form action potentials, i.e. the neurons involved fire in an excessively synchronous manner. In addition, the pathological neuron population has an oscillatory neuronal activity, i.e. the neurons fire rhythmically. In the case of neurological or psychiatric disorders, the mean frequency of the pathological rhythmic activity of the affected neuron clusters is approximately in the range from 1 to 30 Hz, but can also be outside this range. In healthy people, however, the neurons fire qualitatively differently, e.g. in an uncorrelated manner.

In FIG. 1, the device 1 is illustrated during CR stimulation. In the brain and/or spinal cord 30 of the patient, at least one neuron population 31 has a pathologically synchronous and oscillatory neuronal activity as described above. The stimulation unit 11 generates sensory stimuli 22 that are received by the patient and are transmitted to the pathologically active neuron population 31 in the brain and/or spinal cord 30 via the nervous system. The stimuli 22 are designed such that the delayed (or phase-shifted) stimulation via at least two stimulation channels effects a desynchronization of the pathologically synchronous activity of the neuron population 31. A reduction in the coincidence rate of the neurons caused by the stimulation can lead to a reduction of the synaptic weights and thus to a "forgetting" of the tendency to produce pathologically synchronous activity.

The stimuli 22 administered in the CR stimulation effect a so-called reset of the phase of the neuronal activity of the stimulated neurons in the neuron population 30. As a result of the reset, the phase of the stimulated neurons is set to or close to a specific phase value, e.g. 0°, independent of the current phase value (in practice, it is not possible to exactly set a specific phase value, however, this is not required for a successful CR stimulation). Thus, the phase of the neuronal activity of the pathological neuron population 31 is controlled by means of a targeted stimulation. Since the pathological neuron population 31 is stimulated at different points via the stimulation channels 12 to 15, the phases of the neuronal activity of the subpopulations 32 to 35 of the pathological neuron population 31 illustrated in FIG. 1 can be reset at different points in time by applying the stimuli 22 in a delayed (or phase-shifted) manner via the stimulation channels 12 to 15. As a result, the pathological neuron population 31, the neurons of which have been active synchronously and with the same frequency and phase previously, is split into several subpopulations with different phases. For example, the subpopulation 32 is stimulated via the stimulation channel 12, the subpopulation 33 is stimulated via the stimulation channel 13, the subpopulation 34 is stimulated via the stimulation channel 14 and the subpopulation 35 is stimulated via the stimulation channel 15. Within each of the subpopulations 32 to 35, the neurons continue to be synchronous after the phase reset and still fire with the same pathological frequency, but with respect to their neuronal activity, each of the subpopulations 32 to 35 has the phase that has been enforced on it by the stimulus 22 generated in the respective stimulation channel 12 to 15. This means that the neuronal activities of the individual subpopulations 32 to 35, after the reset of their phases, still have an approximately sinusoidal profile with the same pathological frequency, but different phases.

Due to the pathological interaction between the neurons, the state with at least two subpopulations generated by the stimulation is unstable, and the entire neuron population 31 rapidly approaches a state of complete desynchronization, in which the neurons fire in an uncontrolled manner. The desired state, i.e. the complete desynchronization, is thus not immediately present after the delayed (or phase-shifted) application of the phase-resetting stimuli 22, but is usually established within a few periods or even in less than one period of the pathological frequency.

A theory for explaining the success of the stimulation is based on the fact that the desynchronization ultimately desired only becomes possible due to the pathologically increased interaction between the neurons. Here, use is made of a self-organisation process responsible for the pathological synchronization. It has the effect that a division of a total population 31 into subpopulations 32 to 35 with different phases is followed by a desynchronization. In contrast, no desynchronization would occur without a pathologically increased interaction of the neurons.

Furthermore, a reorganization of the connectivity of the disturbed neuronal networks can be achieved by the CR stimulation, so that long-lasting therapeutic effects can be achieved. The achieved synaptic conversion is of great importance for the effective treatment of neurological or psychiatric diseases.

In CR stimulation, the stimuli 22 are usually applied at different points of the brain and/or spinal cord 30 at different times in the course of a so-called sequence. In the above example, exactly one stimulus 22 is generated within a sequence in each of the stimulation channels 12 to 15, so that at each of the different stimulation points exactly one stimulus is applied, i.e. each of the subpopulations 32 to 35 is stimulated exactly once within a sequence. Over a wide range of the stimulus intensity, the CR stimulation with a slowly varying sequence is superior to the CR stimulation with a fixed sequence or with a fast varying sequence, e.g. varying from stimulation cycle to stimulation cycle. In the range of very low stimulus intensities, CR stimulation does not lead to sustainable therapeutic effects, regardless of whether and how the sequence is varied.

If the CR stimulation is applied with a rapidly varying sequence at a very low stimulus intensity, the stimulation leads to a desynchronizing effect, which, however, typically does not last very long after the end of the stimulation. In the case of CR stimulation with a fixed or slowly varying sequence, there is typically no desynchronizing effect at a very low stimulus intensity, neither during nor after the stimulation.

The invention is based on the following surprising observation: A period with a desynchronizing stimulation with a rapidly varying sequence, in the case of a low stimulus intensity, does not have a long-lasting desynchronizing effect itself, but in combination with a period with a desynchronizing stimulation with a slowly varying sequence of a higher stimulus intensity, it causes a long-lasting desynchronizing effect, which is at least equivalent to or even significantly better than the effect achieved by two consecutive periods with a desynchronizing stimulation (with a fixed, rapidly varying or slowly varying sequence) with the higher stimulus intensity.

Consequently, the invention uses a two-stage stimulation, in which the stimulation in the first stage is performed with a rapidly varying sequence at a low stimulus intensity and stimulation in the second stage is performed with a slowly varying sequence at a higher stimulus intensity. In order to realize the two stimulation stages, the stimulation unit 11 can be operated in two different stimulation modes (or operating modes). During at least 75% of the time of a first time interval, the control unit 10 operates the stimulation unit 11 in a first stimulation mode. In the first stimulation mode, the control unit 10 controls the stimulation unit 11 such that the stimulation unit 11 generates sequences of stimuli 22 repetitively and the order of the stimulation channels 12 to 15, in which the stimuli 22 are generated within a sequence, is constant for not more than 5 consecutively generated sequences and is then varied, wherein the strength of the stimuli 22 in the first stimulation mode is less than or equal to a predetermined stimulus intensity. The first time interval is followed by a second time interval. In particular, the second time interval can immediately follow the first time interval, i.e. without an intermediate break. During at least 75% of the time of the second time interval, the control unit 10 operates the stimulation unit in the second stimulation mode. In the second stimulation mode, the control unit 10 controls the stimulation unit 11 such that the stimulation unit 11 generates sequences of stimuli 22 repetitively and the order of the stimulation channels 12 to 15, in which the stimuli 22 are generated within a sequence, is constant for at least 25 consecutively generated sequences and is then varied. The strength of the stimuli 22 in the second stimulation mode is at least 1.3 times the predetermined stimulus intensity.

The stimulation form described above is sufficiently robust so that it is sufficient for the desired stimulation success to operate the stimulation unit 11 for only 75% of the time of the first time interval in the first stimulation mode and for only 75% of the time of the second time interval in the second stimulation mode. Of course, the operating times of the first and second stimulation modes can also be increased in the respective time interval. For example, the stimulation unit 11 can be operated in the first stimulation mode during the complete first time interval and in the second stimulation mode during the complete second time interval. During periods in which the stimulation unit 11 is not operated in the first stimulation mode during the first time interval or in the second stimulation mode during the second time interval, either no stimulation or a stimulation that can be designed in particular differently than the stimulation described in this application can be performed.

Figure 2:
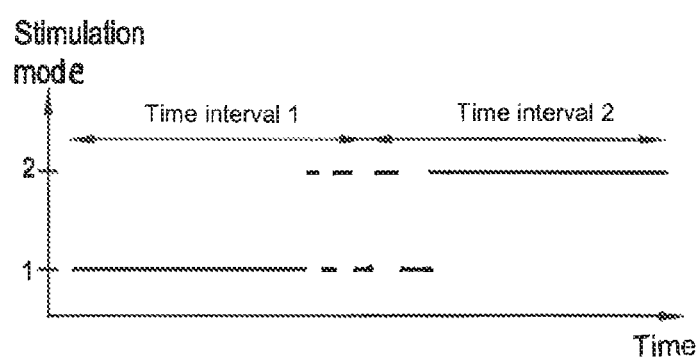
FIG. 2 illustrates a schematic representation of a fractional transition from a first stimulation mode to a second stimulation mode.

It may be advantageous for the patient to not abruptly change from the first stimulation mode to the second stimulation mode, but in a fractionated manner, as is shown by way of example in FIG. 2. An abrupt change from a stimulation intensity below threshold in the first stimulation mode to a stimulation intensity above threshold in the second stimulation mode can be very unpleasant, e.g. painful. In order to make this transition more pleasant, use can be made of habituation effects by switching back and forth several times between the two stimulation modes in the course of the transition from the first time interval to the second time interval. The extent of the side effects, for example pain, does not only depend on the stimulation intensity, but also on the duration of the stimulus application. By applying short periods in the second stimulation mode, the onset of the side effects can be reduced significantly. Even habituation effects can occur, so that the side effects in the later, permanently applied second stimulation mode are less than without the fractionated transition. The duration between switching between the first and second stimulation modes may vary in time, e.g. increase, during the transition, as is shown by way of example in FIG. 2.

Figure 3A:
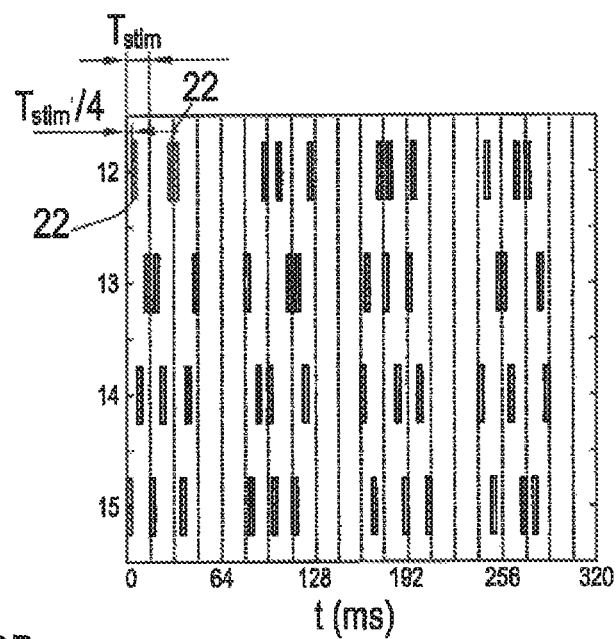
FIG. 3A illustrates a schematic representation of a CR stimulation with rapidly varying stimulus sequences.
Figure 3B:
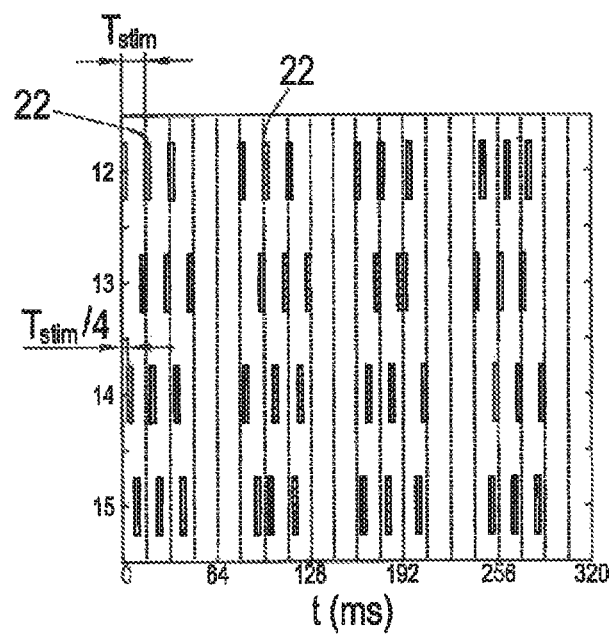
FIG. 3B illustrates a schematic representation of a CR stimulation with slowly varying stimulus sequences.

Embodiments for stimulations in the first and second stimulation modes are shown in FIGS. 3A and 3B.

FIG. 3A shows a CR stimulation, in which in four stimulation channels 12 to 15 repetitive rapidly varying sequences of stimuli 22 are generated in the first stimulation mode. In FIG. 3A, the stimuli 22 generated in the stimulation channels 12 to 15 are plotted against time t. The sequences are generated in a predetermined time pattern consisting of consecutive cycles. The individual cycles are delimited from one another by dashed lines in FIG. 3A. Each cycle has the length $T_{stim}$. In each cycle in which a stimulation is carried out, exactly one sequence of stimuli 22 is generated in the stimulation channels 12 to 15 together, and exactly one stimulus 22 is generated in each stimulation channel 12 to 15, i.e. in the present example, each sequence consists of a succession of four delayed stimuli 22, which are generated in particular in respectively different stimulation channels 12 to 15, wherein the delay can relate in particular to the start times of the stimuli 22. At the beginning of each cycle, in the present example, the order of the stimulation channels 12 to 15, in which the stimuli 22 are generated within the respective sequence, is varied. A different filling of the bars shown in FIG. 3A, which symbolize the stimuli 22, shows a variation of the order. For example, the stimuli 22 in the stimulation channels 12 to 15 are generated in the sequence 15-12-14-13 in the first cycle shown in FIG. 3A. In the second cycle, the order is 15-13-14-12, and in the third cycle the order is 12-15-14-13.

As described above, provision is made for the sequences to remain the same for a maximum of 5 consecutively generated sequences and then to be changed. Furthermore, the variation of the sequences can be performed at a constant rhythm, i.e., a variation always takes place after $i_{Modus\_1}$ cycles, wherein $i_{Modus\_1}$ is an integer from 1 to 5. Alternatively, the number of cycles after which the sequence is varied can be varied according to stochastic or deterministic or mixed stochastic-deterministic rules.

According to one embodiment, in the CR stimulation shown in FIG. 3A, only the order of the stimulation channels 12 to 15 in which the stimuli 22 are generated within the respective sequence is varied. All remaining stimulation parameters can remain constant during the CR stimulation. The variation of the sequences can be performed e.g. stochastically or deterministically or mixed stochastic-deterministically.

Provision may be made for the CR stimulation to take place continuously in the first stimulation mode, i.e. in consecutive cycles, always sequences of stimuli 22 are generated. Alternatively, breaks can also be made during the CR stimulation, in particular during whole cycles. In this way, stimuli 22 may be generated during $n_{Modus\_1}$ consecutive cycles, and no stimuli 22 may generated during the subsequent $m_{Modus\_1}$ cycles, which are designed to desynchronize the pathologically synchronous and oscillatory neuronal activity, wherein $n_{Modus\_1}$ and $m_{Modus\_1}$ are non-negative integers. The pattern of $n_{Modus\_1}$ cycles with stimulation and $m_{Modus\_1}$ cycles without stimulation can be continued periodically. For the exemplary stimulation form shown in FIG. 3A, it holds that $n_{Modus\_1}=3$ and $m_{Modus\_1}=2$.

It is conceivable that other stimuli that are not designed to suppress the pathologically synchronous and oscillatory neuronal activity be applied during the stimulation breaks in particular with the stimulation unit 1. Alternatively, the stimulation unit 11 does not generate any stimuli during the stimulation breaks.

If provision is made for the sequences to be varied after a predetermined number $i_{Modus\_1}$ of sequences ($i_{Modus\_1} \leq 5$), according to one embodiment, the cycles without stimulation are not counted, i.e. in this embodiment, the order of the stimulation channels 12 to 15 in which the stimuli 22 are generated within the respective sequence is not varied until a sequence of stimuli 22 has actually been applied in $i_{Modus\_1}$ cycles in each case.

Each of the four stimulation channels 12 to 15 stimulates a respective one of the subpopulations 32 to 34 of the pathological neuron population 31 shown in FIG. 1. During the maximum of 5 cycles in which the sequences are constant, the stimulus 22 is periodically applied with the period $T_{stim}$ in each of the stimulation channels 12 to 15. The stimuli 22 effect a phase reset of the neuronal activity of the respectively stimulated subpopulation. Furthermore, the time delay between stimuli 22 directly consecutive in time within a sequence and generated in different stimulation channels is $T_{stim}/4$, since in the present embodiment four stimulation channels 12 to 15 are used for CR stimulation. In the general case of P stimulation channels used for the stimulation, the time delay between stimuli 22 directly consecutive in time within a sequence and generated in different stimulation channels would be $T_{stim}/P$ (it is possible to deviate from this value by e.g. up to $\pm 5\%$, $+10\%$ or $\pm 20\%$). The time delay $T_{stim}/P$ may refer to the start times of the stimuli 22. The stimuli 22 generated in different stimulation channels may be identical except for the different start times.

The period $T_{stim}$, which on the one hand indicates the duration of one cycle and on the other hand indicates the period, with which consistent sequences as well as the stimuli 22 generated in a respective stimulation channel 12 to 15 are repeated, may be close to the mean period of the pathological oscillation of the neuron population 31 having the pathologically synchronous and oscillatory neuronal activity or deviate from the mean period by up to $\pm 5\%$, $+10\%$ or $\pm 20\%$. Typically, the frequency $f_{stim}=1/T_{stim}$ is in the range of 1 to 30 Hz. The period of the pathological oscillation of the neuron population 31 to be stimulated can be measured by means of EEG, for example. However, it is also possible to use literature or experience values relating to the respective disease to be treated for the period of the pathological oscillation.

The phase-resetting stimuli 22 may be individual stimuli or also combined stimuli. For example, each stimulus 22 may consist of a train of 2 to 100 pulses, in particular 2 to 10 individual pulses. Within a pulse train, the individual pulses are repeated without interruption at a frequency in the range of 50 to 500 Hz, in particular in the range of 100 to 150 Hz. The pulses of a pulse train may be identical. Depending on the type of stimulation, it may be an acoustic, visual, tactile, vibratory (in particular vibrotactile), thermal, olfactory, gustatoric, transcutaneous electrical, transcutaneous magnetic, transcranial electric and/or transcranial magnetic pulse train and/or an ultrasonic pulse train.

The intensity of the stimuli 22, i.e. the amplitude of the stimuli 22, is less than or equal to a predetermined stimulus intensity in the first stimulation mode. The predetermined stimulus intensity may in particular be below threshold in the sense that the stimuli 22 have desynchronizing effects only during the stimulation, which, however, do not last after the end of the stimulation, i.e. after the end of the stimulation with the stimuli 22 having a stimulus intensity that does not exceed the predetermined stimulus intensity, the desynchronizing effect disappears.

In principle, it can be possible to perform stimulation via an arbitrary number L of stimulation channels by means of the stimulation unit 11 (L>2); however, in the stimulation, stimuli 22 need not necessarily be generated in all L stimulation channels, but the stimuli 22 may also be generated in only a selection of P of the L stimulation channels ($2 \leq P \leq L$), for example. In the case of P stimulation channels, there are P! possible different sequences, wherein in each of these sequences, exactly one stimulus 22 is generated in each of the P stimulation channels. It is conceivable to use all P! possible sequences for the stimulation or to select a subset for the stimulation from the quantity of P! possible sequences. This subset may also vary in time according to stochastic or deterministic or mixed stochastic-deterministic rules. The order of the sequences may be random or be defined before or also during the stimulation.

By the stimulation in the first stimulation mode, the neuron population 31 is brought into a state in which it is clearly more susceptible to the subsequent stimulation in the second stimulation mode with slowly varying sequence and higher stimulus intensity.

Except for the number of cycles after which the sequence is varied and the stimulus intensity, the stimulation in the second stimulation mode may have the same configurations as the stimulation in the first stimulation mode explained above in connection with FIG. 3A. The differences between the stimulation in the second stimulation mode and the stimulation in the first stimulation mode will be explained below with reference to FIG. 3B.

FIG. 3B shows a CR stimulation, in which in the four stimulation channels 12 to 15 repetitive slowly varying sequences of stimuli 22 are generated in the second stimulation mode. The order of the stimulation channels is 12 to 15, in which the stimuli 22 are generated within a sequence, is kept constant for at least 25 consecutively generated sequences and is varied only afterward. It is also conceivable to increase the repetition of the same sequence and to keep the order in which the stimuli 22 are generated in the stimulation channels 12 to 15 per cycle constant in the second stimulation mode for e.g. at least 30 or at least 35 consecutively generated sequences. It should also be noted at this point that in FIG. 3B, for reasons of illustration, the sequences are already varied after less than 25 sequences. However, this is to be understood merely as a simplified representation of a sequence variation that is slow in comparison with FIG. 3A.

In the second stimulation mode, the variation of the sequences can be carried out at a constant rhythm, i.e. a variation always takes place after e.g. $i_{Modus\_2}$ cycles, wherein $i_{Modus\_2} \geq 25$ applies. Alternatively, the number of cycles after which the sequence is varied can be determined according to stochastic or deterministic or mixed stochastic-deterministic rules.

As in the stimulation in the first stimulation mode, only the order of the stimulation channels, in which the stimuli 22 are generated per sequence, may be varied during the stimulation in the second stimulation mode. All remaining stimulation parameters may remain constant during the stimulation.

The variation of the sequences may be effected e.g. stochastically or deterministically or mixed stochastically-deterministically.

The CR stimulation may be carried out continuously in the second stimulation mode, i.e. in consecutive cycles, always sequences of stimuli 22 are generated. Alternatively, breaks can also be made during the CR stimulation, in particular during whole cycles.

In this way, stimuli 22 may be generated during $n_{Modus\_2}$ consecutive cycles, and no stimuli 22 may generated during the subsequent $m_{Modus\_2}$ cycles, which are designed to desynchronize the pathologically synchronous and oscillatory neuronal activity, wherein $n_{Modus\_2}$ and $m_{Modus\_2}$ are non-negative integers. The pattern of $n_{Modus\_2}$ cycles with stimulation and $m_{Modus\_2}$ cycles without stimulation can be continued periodically. For the exemplary stimulation form shown in FIG. 3B, it holds that $n_{Modus\_2}=3$ and $m_{Modus\_2}=2$. The values for $n_{Modus\_2}$ and $m_{Modus\_2}$ of the second stimulation mode may be, but do not have to be identical to the values for $n_{Modus\_1}$ and $m_{Modus\_1}$ of the first stimulation mode.

It is conceivable that other stimuli that are not designed to suppress the pathologically synchronous and oscillatory neuronal activity be applied during the stimulation breaks in particular with the stimulation unit 1. Alternatively, the stimulation unit 11 does not generate any stimuli during the stimulation breaks.

If provision is made for the sequences to be varied after a predetermined number $i_{Modus\_2}$ of sequences ($i_{Modus\_1} \geq 25$), according to one embodiment, the cycles without stimulation are not counted, i.e. in this embodiment, the order of the stimulation channels 12 to 15 in which the stimuli 22 are generated is not varied until a sequence of stimuli 22 has actually been applied in $i_{Modus\_2}$ cycles in each case.

The intensity of the stimuli 22, i.e. the amplitude of the stimuli 22, in the second stimulation mode is at least 1.3 times the predetermined stimulus intensity. The predetermined stimulus intensity may in particular be sufficiently large so that a pronounced and long-lasting therapeutic and/or desynchronizing effect would be achieved if the stimuli 22 were applied during the entire stimulation duration, i.e. during the first and the second time periods. According to one embodiment, the lower limit for the stimulus intensity in the second stimulation mode is greater than 1.3 times the predetermined stimulus intensity and is 1.5 or 1.7 times the predetermined stimulus intensity.

In the two-stage stimulation described here, the stimulus intensity is increased without loss of or restriction to the effectiveness. During the first stage, i.e. in the first stimulation mode, a stimulus intensity below threshold is sufficient, as a result of which undesirable effects can be reduced significantly. By means of the stimulation in the first stimulation mode, the neuron population 31 is brought into a state in which it is clearly more susceptible to the stimulation in the second stimulation mode carried out subsequently in the second stage. The two-stage stimulation consequently enables an improved stimulation effect with side effects and other undesirable effects being reduced.

The underlying active principle of the two-stage stimulation, namely the increase in the desynchronizing effect of the stimulation with slowly varying sequence by means of upstream stimulation with rapidly varying sequence, does not only apply to a below-threshold stimulus intensity of the stimulation with a rapidly varying sequence. Rather, in the case of a first stage above threshold, the effect of the two-stage stimulation at least tends to be better than all other variants of the CR stimulation of the same intensity and duration. However, in the case of the first stage with a stimulus intensity above threshold, the particular advantage is lost that by use of the stimulation below threshold, side effects and other undesirable effects can be avoided or at least reduced.

The device 1 shown in FIG. 1 for stimulating neurons having a pathologically synchronous and oscillatory neuronal activity performs a so-called "open loop" stimulation, i.e. a stimulation without sensors, which are used for feedback and/or control of the stimulation.

Figure 4:
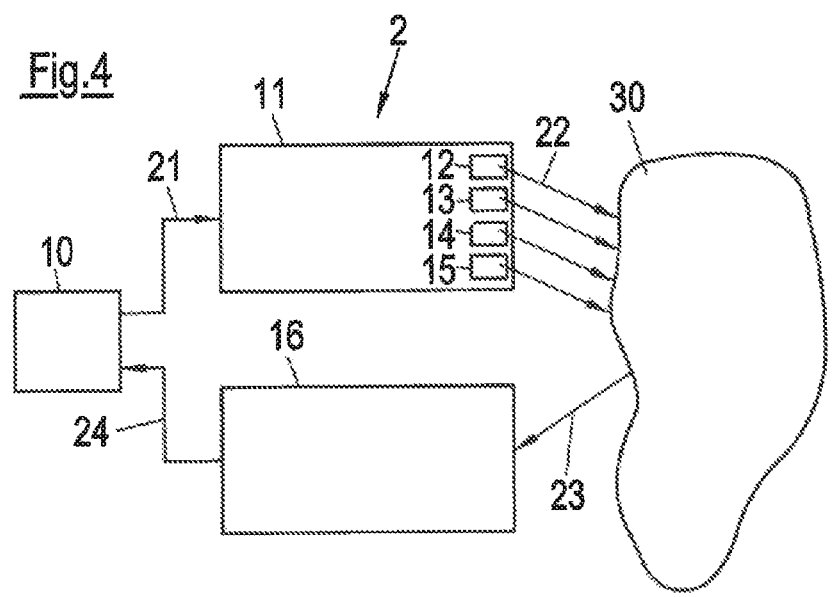
FIG. 4 illustrates a schematic representation of a device for suppressing a pathologically synchronous and oscillatory neuronal activity and in particular for desynchronization of neurons with a pathologically synchronous and oscillatory activity according to a second embodiment.

FIG. 4 schematically shows a device 2 for stimulating neurons with a pathologically synchronous and oscillatory neuronal activity, with which a "closed loop" stimulation can be carried out. The device 2 is a development of the device 1 shown in FIG. 1 and includes, just like the device 1, a control unit 10 and a non-invasive stimulation unit 11, which have the same functions and properties as the above-described control and stimulation units 10, 11 of the device 1.

In addition, the device 2 comprises a measuring unit 16. The stimulation effect achieved by the stimuli 22 is monitored by means of the measuring unit 16. The measuring unit 16 receives one or more measurement signals 23 measured on the patient, converts them into electrical signals 24, if appropriate, and provides them to the control unit 10. In particular, the neuronal activity in the stimulated target region or a region connected to the target region can be measured by means of the measuring unit 16, wherein the neuronal activity of this region correlates sufficiently closely to the neuronal activity of the target region. A non-neural e.g. muscular activity or the activation of the autonomous nervous system can be measured by means of the measuring unit 16 as well, provided that they are sufficiently closely correlated with the neuronal activity of the target region.

The measuring unit 16 includes one or more sensors which in particular make it possible to detect an increase or increase in the amplitude of the pathological oscillatory activity.

Non-invasive sensors may be used as sensors, e.g. chronic or intermittent used electroencephalography (EEG) or electromyography (EMG)) electrodes or magnetoencephalography (MEG) sensors. The neuronal activity may also be determined by detecting characteristic movement patterns, such as tremor, akinesia or epileptic seizures, with the aid of an accelerometer or gyroscope or indirectly by measuring the activation of the autonomous nervous system by means of measuring the skin conduction resistance. It is also possible to use condition values input by the patient into portable devices, such as smart phones, to monitor the success of the stimulation. Such condition values can also be determined by means of short questionnaires.

Alternatively, but less preferably, the sensors can be implanted in the body of the patient. The invasive sensors may be, for example, epicortical electrodes, deep brain electrodes for measuring e.g. local field potentials, sub- or epidural brain electrodes, subcutaneous EEG electrodes and sub- or epidural spinal cord electrodes.

The control unit 10 processes the signals 24, for example the signals 24 can be amplified and/or filtered, and analyzes the processed signals 24. The control unit 10 checks the success of the stimulation on the basis of the measurement signals 23 recorded in response to the application of the stimuli 22.

As soon as a pronounced desynchronization or an acute clinical recovery or a marked improvement of the condition of the patient has been established in particular on the basis of the measurement signals 23 recorded by the measurement unit 16, it is possible to switch from the first stimulation mode to the second stimulation mode in particular with the aid of the control unit 10. In particular, there may be provided an input unit coupled to the control unit 10, which can be operated by the patient and/or the treating physician, and with which it is possible to switch from the first stimulation mode to the second stimulation mode.

The success of the stimulation can in particular be checked by means of a threshold comparison. Depending on which signals are used to determine the success of the stimulation, different threshold comparisons are obtained. If, for example, the pathological neuronal synchronization is measured via the sensors of the measuring unit 16, e.g. EEG electrodes or deep electrodes (as LFP signal), according to experience, lowering of the synchronization by a predetermined value, e.g. by at least 20%, compared to the situation without stimulation is sufficient to establish a sufficient stimulation success and to switch from the first to the second stimulation mode. However, larger values, e.g. 50% and more, can be selected in order to stimulate in the first stimulation mode and thus with lower stimulus intensity for a longer time.

The clinical recovery is determined on the basis of typical changes of clinical scores or questionnaires known to the skilled person. To this end, for example, the values delta S known from the literature are used for a "minimal clinically relevant change", or also larger values, e.g. 2× delta S.

In addition to the above-described control, which determines the switchover from the first to the second stimulation mode, a further control that acts on a slower time scale may be provided. If there is a therapeutic success in a predefined period of time, for example 1 hour, the stimulation is switched off. The success of the therapy is measured as described above, wherein the threshold values can be preset by the user for a sufficient therapeutic success, for example a reduction of the initial synchronization by 80%. If these threshold values are exceeded again for a predefined period, e.g. 60 s, and/or the patient reports a condition that is no longer sufficiently improved, the two-stage stimulation is restarted as described above.

By means of the measuring unit 16 of the device 2, it is possible to estimate values for the lengths of the first time interval and of the second time interval for a respective patient, which are required to achieve the desired stimulation success. Subsequently, said information can be used for use with the device 1, which does not have a measuring unit. In principle, the lengths of the first and second time intervals can be in the minute or hour range.

Furthermore, the predetermined stimulus intensity, from which the upper or lower limit for the stimulus intensities in the first and second stimulation modes is obtained, can be determined with the aid of the measuring unit 16 according to one embodiment. This information can then also be used in an application using the device 1. In order to determine the predetermined stimulus intensity, the stimulation unit 11 is operated in the first stimulation mode, for example, and the intensity of the stimuli 22 is increased starting from zero until an acute effect is established, i.e. a reduction of the synchronization of the stimulated neuron population 31, which however disappears again after completion of the stimulation. The predetermined stimulus intensity can be derived from the stimulus intensity thus obtained by selecting the predetermined stimulus intensity e.g. from a range, the lower limit of which is the stimulus intensity at which a reduction of the synchronization of the stimulated neuron population starts, and the upper limit of which is e.g. 1.1 times the above stimulus intensity.

The individual components of the devices 1 and 2, in particular the control unit 10, the stimulation unit 11 and/or the measuring unit 16, may be structurally separated from one another. The devices 1 and 2 can therefore also be regarded as systems. In order to carry out its tasks, the control unit 10 may include a processor, for example a microcontroller. The stimulation methods described herein may be stored as software code in a memory associated with the control unit 10.

Figure 5:
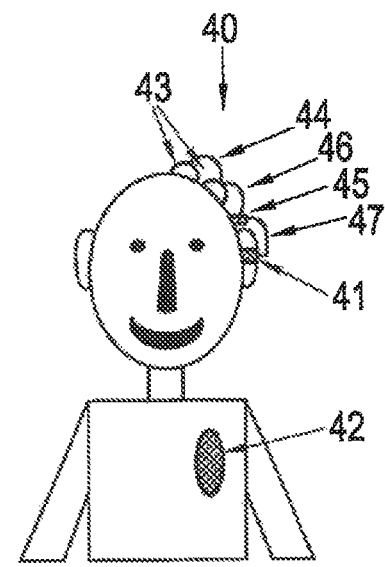
FIG. 5 illustrates a schematic representation of a device for the acoustic stimulation of neurons having a pathologically synchronous and oscillatory neuronal activity.

FIG. 5 schematically shows a device 40 for the non-invasive acoustic stimulation of neurons having a pathologically synchronous and oscillatory neuronal activity according to an embodiment of the invention. Acoustic stimuli, in particular acoustic CR stimuli, are administered to the patient via ear or headphones 41 or differently configured loudspeakers, wherein an earphone is a loudspeaker placed in the ear canal. The control signals used for this purpose are generated by a control unit 42. Non-invasively fixed EEG electrodes 43, which are connected via a cable 44, serve for "closed loop" stimulation. The corresponding calculation is carried out in a small component 45, which preferably includes a measuring amplifier and is connected to the EEG electrodes 43 or the ear or headphones 41 via cables 46, 47, and/or in the actual control unit 42 accommodating the battery or the rechargeable battery. The control unit 42 and the component 45 are telemetrically connected to one another in the embodiment illustrated in FIG. 5; in this case, the component 45 (or a component connected to it via cables) also includes a battery or a rechargeable battery. Alternatively, the control unit 42 and the component 45 may also be connected to one another via cables, so that the component 45 is fed via the power supply from the control unit 42.

If the stimuli 22 described herein are acoustic stimuli 22, the stimulus intensity is determined by the volume of the stimuli 22.

Figure 6:
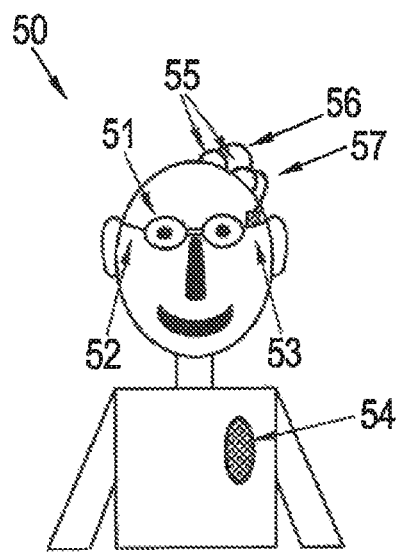
FIG. 6 illustrates a schematic representation of a device for the visual stimulation of neurons having a pathologically synchronous and oscillatory neuronal activity.

FIG. 6 schematically shows a device 50 for the non-invasive visual stimulation of neurons having a pathologically synchronous and oscillatory neuronal activity according to an embodiment of the invention. In this embodiment, the patient wears stimulation spectacles 51, which, for example, are attached to the head of the patient by means of earpieces 52. A component 53 includes a calculating and telemetry unit. The latter serves for connection with the actual control unit 54 accommodating the battery or rechargeable battery. The component 53 and the control unit 54 are telemetrically connected to one another; in this case, the component 53 (or a component connected to it via cables) likewise includes a battery or a rechargeable battery. Alternatively, the component 53 and the control unit 54 may also be connected to one another via cables. Non-invasively fixed EEG electrodes 55 serve for "closed loop" stimulation. The EEG electrodes 55 are connected to the component 53 via cables 56, 57.

The visual stimuli generated by the stimulation spectacles 51 can be based on a luminosity or brightness variation (or variation of the light intensity or luminous intensity), for example, they can be applied as pulses or as sequences of pulses with varied luminosity or brightness. Depending on the configuration, the visual stimuli can be applied as luminosity modulation of natural visual stimuli, e.g. by means of homogeneous or segmented transmission spectacles, in which the transmission can be regulated in a voltage-dependent manner, as a modulated visual stimulus in addition to a natural visual stimulus, e.g. by means of partially transparent light spectacles, or as an artificial visual brightness stimulus, e.g. by means of opaque light spectacles. The stimulation spectacles 51 are preferably divided into different segments, the luminosity or transmission or brightness of which can be controlled separately in order to be able to stimulate different points of the retina independently of one another.

Figure 7:
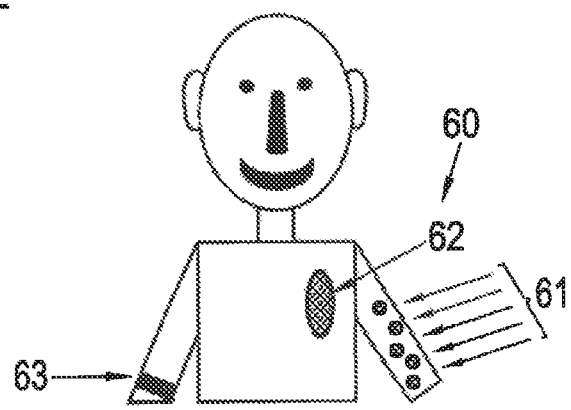
FIG. 7 illustrates a schematic representation of a device for the tactile, vibratory, thermal, transcutaneous electrical and/or transcutaneous magnetic stimulation and/or ultrasonic stimulation of neurons having a pathologically synchronous and oscillatory neuronal activity.

FIG. 7 schematically shows a device 60 for the non-invasive tactile, vibratory, thermal, transcutaneous electrical and/or transcutaneous magnetic stimulation and/or ultrasonic stimulation of neurons having a pathologically synchronous and oscillatory neuronal activity according to an embodiment of the invention. The device 60 comprises a stimulation unit 61, a control unit 62 controlling the stimulation unit 61, and an accelerometer 63 for recording measurement signals. The stimulation unit 61 and the accelerometer 63 may be connected to the control unit 62 in a telemetric manner or via cables.

The stimulation unit 61 comprises a plurality of stimulation elements for generating tactile, vibratory, thermal, transcutaneous electrical and/or transcutaneous magnetic stimuli and/or ultrasonic stimuli. The stimulation elements are designed such that they can be placed on the skin of the patient. Depending on the disease or the affected body parts, the stimulation elements are attached to the skin of the patient in a suitable arrangement, for example to the arm, the leg, the hand and/or the foot of the patient. The plurality of stimulation elements makes it possible to stimulate different receptive regions of the skin via the individual stimulation elements in a temporally and spatially coordinated manner.

Stimulation elements for generating tactile and/or vibratory stimuli are, for example, vibration actuators, which press into the patient's skin at a frequency in the range of 1 to 300 Hz and in particular 1 to 60 Hz and preferably 100 to 300 Hz and thereby generate the desired stimuli. In the case of vibration actuators, the stimulus intensity is determined by the amplitude of the vibration actuators. Stimulation elements for generating thermal stimuli may be lasers or differently configured elements for generating heat, in particular heat radiation, for example. Here, the stimulus intensity is determined by the temperature generated with the thermal stimuli.

In order to generate transcutaneous electrical stimuli, electrodes are typically attached to the skin of the patient. Transcutaneous magnetic stimuli can be generated by corresponding stimulation elements for generating magnetic stimuli, in particular by current-conducting coils. Ultrasonic stimuli are generated by stimulation elements for generating ultrasonic waves. In the above stimulation modalities, the stimulus intensity is determined by the current intensity of the transcutaneous electrical stimuli, the magnetic field strength or amplitude of the ultrasonic waves generated by the magnetic stimuli at the stimulation point.

In the application of acoustic or visual stimuli, said stimuli are perceived via at least one ear or at least one eye of the patient. The tactile, vibratory, thermal, transcutaneous electrical and/or transcutaneous magnetic stimuli and/or ultrasonic stimuli can be received by receptors located in or under the skin, and be transmitted to the nervous system. These receptors include, for example, Merkel cells, Ruffini corpuscles, Meissner corpuscles and hair follicle receptors, which act in particular as receptors for the tactile stimuli. The vibratory stimuli are predominantly aimed at the depth sensitivity. The vibratory stimuli can be received by receptors located in the skin, the muscles, the subcutaneous tissue and/or the tendons of the patient. Examples of receptors for the vibratory stimuli include, by way of example, the Pacinian corpuscles, which impart vibration sensations and accelerations. The thermal stimuli are absorbed by the thermoreceptors of the skin. These are hot receptors (also called heat receptors, hot sensors or heat sensors) and cold sensors (also called cold sensors or cold receptors).

In the skin of humans, the cold sensors are located more skin-deep, the hot receptors are located somewhat deeper. The transcutaneous electrical and transcutaneous magnetic stimuli as well as the ultrasonic stimuli do not specifically act on only one group of receptors located in or under the skin, and can also directly stimulate nerve fibers.

The targeted stimulation of specific regions of the brain or spinal cord is made possible by the tonotopic or somatotopic assignment of body areas to these regions. For example, acoustic stimuli in the inner ear are converted into nerve pulses and transmitted to the auditory cortex via the auditory nerve. Due to the tonotopic arrangement of the auditory cortex, a specific part of the auditory cortex is activated during the acoustic stimulation of the inner ear at a specific frequency.

During visual stimulation, different points in the visual field are imaged onto different points of the retina via the lens of the eye. The different points of the retina are in turn connected to different neurons in the brain via the optic nerve. Consequently, different neurons can be stimulated with the stimuli applied at different spatial locations.

Furthermore, due to the somatotopic structure of the nerve conduction paths and associated regions of the brain, different neurons are stimulated by tactile, vibratory, thermal, transcutaneous electrical and/or transcutaneous magnetic stimuli and/or ultrasonic stimuli, which are applied at different points of the skin. With these stimulation forms, the stimulation elements can be applied e.g. to the foot, lower leg and thigh or also to the hand, the forearm and the upper arm of the patient, in order to thereby be able to stimulate specific neurons.

In the gustatoric stimulation, different regions of the tongue are stimulated with the corresponding taste qualities—sweet, sour, salty, bitter and umami (Japanese for a savory, spicy, bouillon-like flavor). However, it is also possible to electrically stimulate the tongue. In this case, primarily the mucous membrane is stimulated, which activates a considerably large representation, i.e. a considerably large associated area in the homunculus (representation of the surface of the human in the sensomotoric cortex). Due to the somatotopic structure of the nerve conduction paths and associated regions of the brain, different neurons are stimulated by gustatoric stimuli, which are applied at different points of the tongue.

The following applies very generally and not only with respect to the embodiments described herein. In the acoustic stimulation, each stimulation channel is assigned to a respective different frequency range, from which the tones that are applied as acoustic stimuli in the respective stimulation channel are selected. In the visual stimulation, the stimulation channels are determined by different points or areas in the visual field of the patient. The visual stimuli generated in a respective stimulation channel are generated at a respective point or in a respective region of the visual field. The stimulation channels of the tactile, vibratory, thermal, transcutaneous electrical and/or transcutaneous magnetic stimuli and/or ultrasonic stimuli are determined by the parts of the skin that are stimulated with the respective stimulation elements. Consequently, each stimulation channel is assigned to a respective part or a respective region of the skin.

The stimulation channels of the gustatoric stimuli are determined by the points of the tongue that are stimulated with the corresponding taste qualities or electrical stimuli. In the case of olfactory stimulation, psychophysically sufficiently disjunct odor stimuli are used, by means of which the stimulation channels would be defined. The psychophysically sufficiently disjunct odor stimuli might be personalized, i.e. adapted to the individual patient.

In the transcranial electrical and transcranial magnetic stimulation, electrodes or magnetic field generators, in particular current-conducting coils, are attached to the body, in particular to the head of the patient. By the electrodes and magnetic field generators, currents or magnetic fields can be generated in the brain and/or spinal cord of the patient, wherein the strength of these currents or magnetic fields indicates the stimulus intensity. Depending on the application location of the electrodes or magnetic field generators, different target regions in the brain and/or spinal cord can be stimulated. Consequently, the stimulation channels are determined by the areas of the patient's body to which the electrodes or magnetic field generators are attached.

Accordingly, the stimulation unit described above can stimulate different regions of the brain or spinal cord separately via different stimulation channels by transmitting the applied stimuli via nerve lines to different target regions in the brain and/or spinal cord. The target regions may be stimulated possibly with different and/or delayed stimuli during the stimulation.

As described above, in the case of the CR stimulation, the stimuli 22 bring about a so-called reset of the phase of the neuronal activity of the stimulated neurons. The phase reset of the individual stimuli 22 can be checked by means of the measurement signals 23 recorded by the measuring unit 16. Such an examination can be carried out prior to the actual therapeutic two-stage neurostimulation.

For this purpose, a signal that sufficiently represents the activity of the subpopulation stimulated via the $j^{th}$ stimulation channel is measured via a sensor of the measuring unit 16. This signal is obtained either directly from the subpopulation by means of a non-invasive measurement, for example via EEG or MEG electrodes, or an invasive measurement, e.g. via implanted electrodes, as surface EEG or as local field potential via depth electrodes. The signal can also be determined indirectly via by measuring a variable correlated with the activity of the stimulated subpopulation. For this purpose, e.g. EEG/MEG/LFP signals of the neuronal activity of a different neuron population, which is closely coupled to this subpopulation, or associated electromyography, accelerometer or gyroscope signals are suitable.

Since neuronal signals typically include rhythmic activity in different frequency bands, it is advantageous in such cases to determine the signal $x_j(t)$, which represents the pathological oscillatory activity of the subpopulation stimulated by the $j^{th}$ stimulation channel, for example by means of bandpass filtering or wavelet analysis or empirical mode decomposition A hardly complex procedure to check a phase reset consists in a determination of the averaged stimulus response. To this end, a stimulus with identical stimulus parameters is applied at the times $\tau_1, \tau_2, \ldots, \tau_l$. The intervals between the individual stimuli $\tau_{k+1}-\tau_k$ should be sufficiently large and randomized, i.e. not constant, in order to avoid transient responses (cf. P. A. Tass: Transmission of stimulus-locked responses in two coupled phase oscillators. Phys. Rev. E 69, 051909-1-24 (2004)). The intervals $\tau_{k+1}-\tau_k$ should typically be in the range of at least ten times, better one hundred times the mean period of the pathological oscillation. The stimulus response averaged over all l test stimuli is calculated according to the following equation:

$$\bar{x}_j(t) = \frac{1}{l}\sum_{k=1}^{l}(\tau_k + t) \quad (1)$$

If the intervals $\tau_{k+1}-\tau_k$ between the individual stimuli are sufficiently large, no averaged stimulus response is obtained in the pre-stimulus area, i.e. in the area before the application of a respective stimulus (cf. P. A. Tass: Transmission of stimulus-locked responses in two coupled phase oscillators. Phys. Rev. E 69, 051909-1-24 (2004)). A phase reset can be determined if an averaged stimulus response can be detected, i.e. if a stimulus response different from zero can be found in the post-stimulus area, i.e. in the area for t>0, where t=0 represents the starting time of the respective stimulus. This can be determined by visual inspection. This can also be carried out by the device 2, in particular the control unit 10, by considering the pre-stimulus distribution of $\bar{x}_j(t)$ or $|\bar{x}_j(t)|$ and determining a characteristic threshold value, for example the $99^{th}$ percentile of the pre-stimulus distribution of $|\bar{x}_j(t)|$ or simply the maximum thereof. If, for example, the amount of the post-stimulus response exceeds this characteristic threshold value for a predetermined minimum period, for example 20 ms, as a matter of principle, an averaged response different from zero is present. In this case, a phase reset can be present. That is, the stimulus intensity would have to be increased until the post-stimulus response differs from a zero line. In addition to the simple method presented here, which has proven its worth in practice, other statistical tests known to the skilled person can be used for signal analysis as well.

A more precise but more complex variant for examining whether the stimuli bring about a phase reset, is the analysis of phase. To this end, the phase $\psi_j(t)$ of $x_j(t)$ is determined. This is carried out by means of a Hilbert transform of the signal representing the pathological oscillatory activity, which is determined by means of bandpass filtering or empirical mode decomposition. In comparison to bandpass filtering, the empirical mode decomposition enables a parameter-independent determination of physiologically relevant modes different frequency ranges (cf. N. E. Huang et al.: The empirical mode decomposition and the Hilbert spectrum for nonlinear and non-stationary time series analysis. Proc. R. Soc. A: Math. Phys. Eng. Sci. 454:903-995 (1998)). The combination of empirical mode decomposition with the below Hilbert transform is referred to as Hilbert-Huang transform (cf. N. E. Huang et al.: A confidence limit for the empirical mode decomposition and Hilbert spectral Analysis, Proceedings of the Royal Society of London Series A, 459, 2317-2345 (2003)). The phase $\psi_j(t)$ can also be determined by means of wavelet analysis.

A phase reset is present if the phase $\psi_j(t)$ is set to a preferred value by a stimulus (with the start of the stimulus at t=0) after a certain time. That is, $\{\psi_j(\tau_k+t)\}_{k=1,\ldots,l}$, the distribution of the values of the phase $\psi_j(t)$ obtained from the l stimulus responses has an accumulation value at the time t (relative to the burst start at t=0). The person skilled in the art knows different methods with which it is possible to establish that a distribution has an accumulation value (i.e. a peak). A common method is the determination of the phase reset index $\rho(t)$ by means of a circular average:

$$\rho(t) = \left|\frac{1}{l}\sum_{k=1}^{l}\exp[i\psi_j(\tau k + t)]\right| \quad (2)$$

A phase reset is present if ρ(t) exceeds the maximum or the 99$^{th}$ percentile of the pre-stimulus distribution of ρ(t) (at a point in time or within a small time window of e.g. 20 ms width), for example.

In practice, the analysis with the averaged responses $\bar{x}_j(t)$ has proven to be sufficient.

FIGS. 8 to 11 illustrate the effects that can be achieved with the invention described herein on the basis of simulation results. The simulation is based on a network of 200 neurons, wherein all neurons among each other have a strong exciting short-range coupling with one another and a weak inhibiting long-range coupling. The synaptic coupling strengths in the network may change according to STDP (spike timing dependent plasticity) rules. An initially highly coupled network produces highly synchronous neuronal activity.

Figure 8:
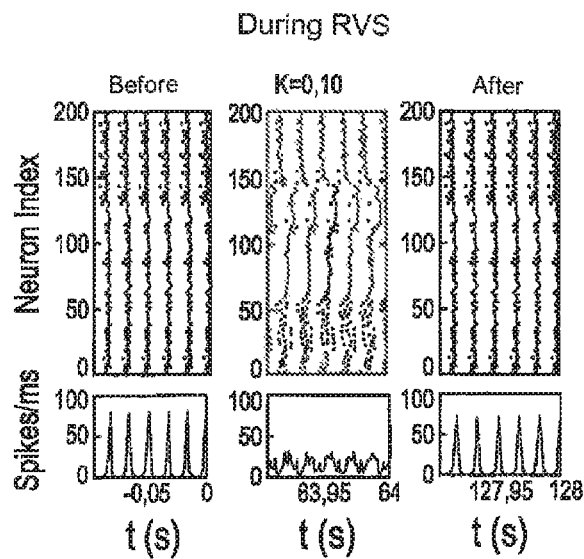
FIG. 8 to 11 illustrate diagrams with simulation results for various CR stimulations.
Figure 9:
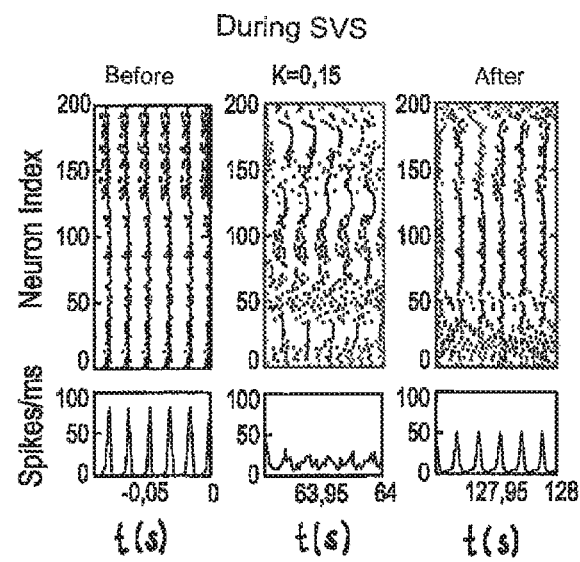

For the simulations shown in FIGS. 8 and 9, the respective CR stimulation was started at t=0 s and terminated at t=64 s. The activity of the network was examined until t=128 s, i.e. up to 64 s after the end of the stimulation. During the CR stimulation, stimulation was carried out continuously, i.e. without cycles in which breaks were made.

In FIGS. 8 and 9, the images in the upper row respectively show the time at which each individual neuron fires during different time intervals: before, during and after the application of the CR stimulation. The left column shows the neuronal activity during the last 80 ms before the beginning of the CR stimulation. The central column shows the neuronal activity during the last 80 ms of the CR stimulation, and the right column relates to the last 80 ms at the end of the subsequent stimulation-free period, which lasts 64 s. The images in the upper row are raster plots of the neuronal activity, i.e. electrical discharges of the individual neurons are marked as points. The images in the lower row respectively show how many neurons fire at the same time within 1 ms during the respective periods of time.

For the simulation shown in FIG. 8, a CR stimulation with rapidly varying sequence and below-threshold stimulus intensity (RVS) was used. The selected stimulus intensity was K=0.10. For the simulation shown in FIG. 9, a CR stimulation with slowly varying sequence and above-threshold stimulus intensity (SVS) was used, wherein the stimulus intensity was K=0.15 and each sequence was repeated 100 times before a new sequence was applied. The network was in the same initial state before the application of the CR stimulations in FIGS. 8 and 9.

As can be seen from the center column of FIG. 8, the rapidly varying CR stimulation with low stimulus intensity is sufficient for an acute effect, in which the degree of synchronization decreases during the CR stimulation and significantly increases again after the termination of the CR stimulation. However, the sole application of a slowly varying CR stimulation with a higher stimulus intensity, which is shown in FIG. 9, does not lead to persistent desynchronization.

Figure 10:
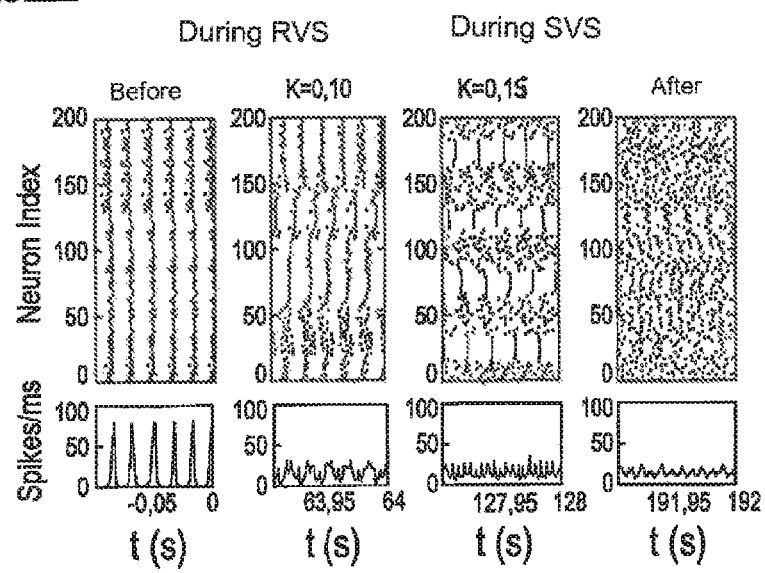

For the simulation shown in FIG. 10, the CR stimulations of FIGS. 8 and 9 were combined with one another. In FIG. 10, the first column from the left shows the neuronal activity during the last 80 ms before the beginning of the CR stimulation. The second column shows the neuronal activity during the last 80 ms of the CR stimulation with rapidly varying sequence and below-threshold stimulus intensity. The third column shows the neuronal activity during the last 80 ms of the CR stimulation with slowly varying sequence and above-threshold stimulus intensity. The fourth column relates to the last 80 ms at the end of the subsequent stimulation-free period, which lasts 64 s. The same stimulation parameters as in FIGS. 8 and 9 were used.

Surprisingly, it is found that due to the CR stimulations with rapidly varying sequence and slowly varying sequence being applied rapidly one after the other, a stimulation success is achieved that still persists after 64 s after the end of the CR stimulation.

Figure 11:
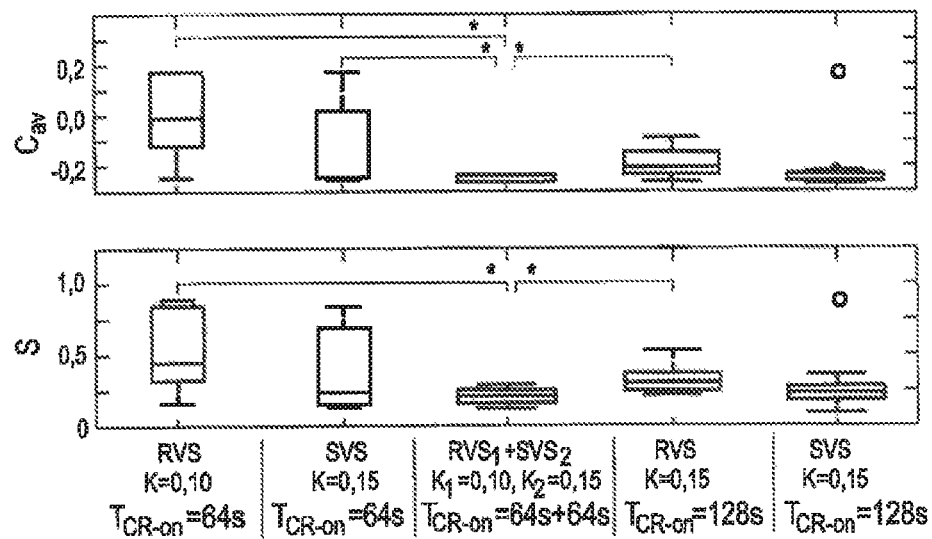

Since the initial conditions of the network and the orders of the consecutive sequences influence the desynchronization, the simulations were repeated for ten other combinations of initial conditions of the network and sequence orders. In FIG. 11, the distributions $C_{av}$ of the resulting mean values of the synaptic strength and the distributions S of the synchronization after the termination of the CR stimulation are shown for a stimulation duration of 64 s (two left columns) or 128 s (three right columns) as box plots for five different combinations of CR methods and stimulus intensities K. The total duration of the CR stimulation is referred to as a $T_{CR\text{-}on}$. The medians of the resulting $C_{av}$ and S distributions are illustrated by the horizontal lines in the boxes. The box corresponds to the range in which the middle 50% of the data are, the antennas ("whiskers") correspond to the lower or upper 25% of the data. Open circles denote outliers and are defined as values that are at least 1.5 times the length of the box below or above the box. A star indicates that the two-stage stimulation (middle column) with an initial CR stimulation with rapidly varying sequence and below-threshold stimulus intensity and a subsequent CR stimulation with slowly varying sequence and above-threshold stimulus intensity is statistically significantly more successful than the one-stage stimulation that lasts 64 s or 128 s (one-sided Mann-Whitney-U-test, p<0.05).

The invention claimed is:

1. A device for stimulating neurons, comprising:
   a non-invasive stimulation unit configured to generate stimuli in a plurality of stimulation channels, such that the stimuli stimulate a neuron population in at least one of a brain and a spinal cord of a patient via the stimulation channels at respectively different points on the patient; and
   a control unit configured to operate the stimulation unit during a first time interval and a second time interval following the first time interval in different stimulation modes,
   wherein the control unit controls the stimulation unit during at least 75% of a duration of the first time interval in a first stimulation mode such that the stimulation unit repetitively generates sequences of stimuli and an order of the stimulation channels in which the stimuli are generated within a sequence is constant for not more than 5 successively generated sequences and then varied,
   wherein the control unit controls the stimulation unit during at least 75% of a duration of the second time interval in a second stimulation mode such that the stimulation unit repetitively generates sequences of stimuli and an order of the stimulation channels in which the stimuli are generated within a sequence is constant for at least 25 successively generated sequences and then varied, and
   wherein an intensity of the stimuli in the first stimulation mode is lower than or equal to a predetermined stimulus intensity and the intensity of the stimuli in the second stimulation mode is at least 1.3 times the predetermined stimulus intensity.

2. The device according to claim 1, wherein the sequences in at least one of the first and second stimulation mode are generated in a time pattern of consecutive cycles and at least in some of the cycles a sequence of stimuli is generated respectively.

3. The device according to claim 2, wherein, within a respective cycle, either exactly one sequence of stimuli is generated or no stimuli are generated.

4. The device according to claim 2, wherein the stimuli are generated during n consecutive cycles and no stimuli are generated during subsequent m cycles such that a pattern of the n consecutive cycles followed by the m cycles is periodically continued, wherein n and m are non-negative integers.

5. The device according to claim 1, wherein a pattern according to which an order in which the stimulation unit generates the stimuli in the plurality of stimulation channels within a sequence in the first stimulation mode is constant for at most 5 consecutively generated sequences and then varied is repeated multiple times.

6. The device according to claim 1, wherein a pattern according to which an order in which the stimulation unit generate the stimuli in the plurality of stimulation channels within a sequence in the second stimulation mode is constant for at least 25 consecutively generated sequences and then varied is repeated multiple times.

7. The device according to claim 1, wherein the stimuli are configured to desynchronize a pathologically synchronous and oscillatory activity of the neuron population when being administered to the patient via the plurality of stimulation channels.

8. The device according to claim 7, wherein a duration of a cycle substantially corresponds to a mean period of pathological oscillation of the neuron population.

9. The device according to claim 7, wherein the stimulation unit is configured such that the stimuli generated in a respective stimulation channel stimulate a respective subpopulation of the neuron population and reset a phase of the neuronal activity of said sub population.

10. The device according to claim 1, wherein the stimulation unit is configured to generate exactly one stimulus within a respective sequence in each stimulation channel.

11. The device according to claim 10, wherein the one stimulus is exactly one pulse train.

12. The device according to claim 1, further comprising a measuring unit configured to record measurement signals for a neuronal activity of the neuron population stimulated with the stimuli.

13. The device according to claim 12, wherein the control unit is configured to switch from the first stimulation mode to the second stimulation mode when the control unit determines, based on the recorded measurement signals, that a degree of synchronization of the stimulated neuron population is reduced by at least one predetermined threshold value when the stimuli are applied in the first stimulation mode.

14. The device according to claim 1, wherein the stimuli are at least one of acoustic, visual, tactile, vibratory, thermal, olfactory, gustatoric, transcutaneous electrical, transcutaneous magnetic, transcranial electrical stimuli, transcranial magnetic stimuli and ultrasonic stimuli.

15. A method for stimulating neurons by a non-invasive stimulation unit that generates stimuli in a plurality of stimulation channels such that the stimuli stimulate a neuron population in at least one of a brain and a spinal cord of a patient via the stimulation channels at respectively different points of the patient, the method comprising:

operating the stimulation unit in different stimulation modes during a first time interval and a second time interval following the first time interval;

operating the stimulation unit in a first stimulation mode during at least 75% of a duration of the first time interval such that the stimulation unit repetitively generates sequences of stimuli and an order of the stimulation channels in which the stimuli are generated within a sequence is constant for not more than 5 successively generated sequences and then varied; and operating the stimulation unit in a second stimulation mode during at least 75% of a duration of the second time interval such that the stimulation unit repetitively generates sequences of stimuli and an order of the stimulation channels in which the stimuli are generated within a sequence is constant for at least 25 successively generated sequences and then varied, wherein an intensity of the stimuli in the first stimulation mode is lower than or equal to a predetermined stimulus intensity and an intensity of the stimuli in the second stimulation mode is at least 1.3 times the predetermined stimulus intensity.

16. The method in accordance with claim 15, further comprising recording, by a measuring unit, measured signals that reproduce a neuronal activity of the neurons stimulated by the stimuli.

17. The method in accordance with claim 16, further comprising switching from the first stimulation mode to the second stimulation mode when the recorded measured signals indicate that a degree of synchronization of the stimulated neurons is reduced by at least one predefined threshold value when the stimuli are applied in the first stimulation mode.

18. A tangible, non-transitory computer program product for execution in a data processing system, the tangible, non-transitory computer program product including instructions, which when executed by the data processing system, provide for:

generating control signals for controlling a non-invasive stimulation unit to generate stimuli in a plurality of stimulation channels that stimulate a neuron population in at least one of a brain and a spinal cord of a patient via the stimulation channels at respectively different points of the patient;

operating the stimulation unit in different stimulation modes during a first time interval and a second time interval following the first time interval;

operating the stimulation unit in a first stimulation mode during at least 75% of a duration of the first time interval such that the stimulation unit repetitively generates sequences of stimuli and an order of the stimulation channels in which the stimuli are generated within a sequence is constant for not more than 5 successively generated sequences and then varied; and operating the stimulation unit in a second stimulation mode during at least 75% of a duration of the second time interval such that the stimulation unit repetitively generates sequences of stimuli and an order of the stimulation channels in which the stimuli are generated within a sequence is constant for at least 25 successively generated sequences and then varied, wherein an intensity of the stimuli in the first stimulation mode is lower than or equal to a predetermined stimulus intensity and an intensity of the stimuli in the second stimulation mode is at least 1.3 times the predetermined stimulus intensity.

\* \* \* \* \*